US00PP15676P2

(12) United States Plant Patent
Dümmen

(10) Patent No.: US PP15,676 P2
(45) Date of Patent: Mar. 15, 2005

(54) ***GERANIUM* PLANT NAMED 'DUECORONA'**

(50) Latin Name: *Pelargonium×hortorum*
Varietal Denomination: Duecorona

(75) Inventor: Marga Dümmen, Rheinberg (DE)

(73) Assignee: Dümmen Jungpflanzen Gbr., Rheinberg (DE)

( * ) Notice: Subject to any disclaimer, the term of this patent is extended or adjusted under 35 U.S.C. 154(b) by 0 days.

(21) Appl. No.: 10/859,521

(22) Filed: Jun. 1, 2004

(51) Int. Cl.[7] ..... A01H 5/00
(52) U.S. Cl. ..... Plt./330
(58) Field of Search ..... Plt./330

(56) References Cited

PUBLICATIONS

UPOV–Rom hitson 'Duecorona', Plant Variety Database, GTI Jouve Retrieval software, 2004/02.*

* cited by examiner

*Primary Examiner*—Anne Marie Grunberg
(74) *Attorney, Agent, or Firm*—C. A. Whealy

(57) ABSTRACT

A new and distinct cultivar of Zonal Geranium plant named 'Duecorona', characterized by its upright, somewhat outwardly spreading and rounded plant habit; freely branching habit; dark green-colored foliage; freely and early flowering habit; and bright red-colored semi-double flowers.

1 Drawing Sheet

Botanical classification/cultivar denomination: *Pelargonium×hortorum* cultivar Duecorona.

BACKGROUND OF THE INVENTION

The present invention relates to a new and distinct cultivar of Zonal Geranium plant, botanically known as *Pelargonium×hortorum,* and hereinafter referred to by the name 'Duecorona'.

The new Zonal Geranium is a product of a planned breeding program conducted by the Inventor in Rheinberg, Germany. The objective of the breeding program was to develop new freely and early flowering Zonal Geraniums with attractive flower and foliage colors.

The new Zonal Geranium originated from an open pollination made by the Inventor in May, 1998, of two unknown selections of *Pelargonium hortorum,* not patented. The cultivar Duecorona was discovered and selected by the Inventor as a flowering plant within the progeny from this stated an open pollination in a controlled environment in Rheinberg, Germany in April, 2001.

Asexual reproduction of the new cultivar by terminal vegetative cuttings at Rheinberg, Germany since July, 2001, has shown that the unique features of this new Zonal Geranium are stable and reproduced true to type in successive generations of asexual reproduction.

SUMMARY OF THE INVENTION

The following traits have been repeatedly observed and are determined to be the unique characteristics of 'Duecorona'. These characteristics in combination distinguish 'Duecorona' as a new cultivar and distinguish it from other known Zonal Geranium cultivars:

1. Upright, somewhat outwardly spreading and rounded plant habit.
2. Freely branching habit.
3. Dark green-colored foliage.
4. Freely and early flowering habit.
5. Bright red-colored semi-double flowers.

The new Zonal Geranium can be compared to plants of the cultivar Händel, not patented. In side-by-side comparisons conducted in Rheinberg, Germany, plants of the new Zonal Geranium differed from plants of the cultivar Händel in the following characteristics:

1. Plants of the new Zonal Geranium were taller than plants of the cultivar Händel.
2. Plants of the new Zonal Geranium were more freely branching than plants of the cultivar Händel.
3. Flowers of plants of the new Zonal Geranium were more rounded than flowers of plants of the cultivar H ändel.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Zonal Geranium.

The photograph comprises a side perspective view of a typical flowering plant of 'Duecorona' grown in a container.

DETAILED BOTANICAL DESCRIPTION

The cultivar Duecorona has not been observed under all possible environmental conditions. The phenotype may vary somewhat with variations in environment, such as temperature and light intensity, without, however, any variance in genotype.

The aforementioned photograph, following observations and measurements describe plants grown in Rheinberg, Germany during the summer under commercial practice in a glass-covered greenhouse with day and night temperatures about 18° C. and light levels about 4,500 foot-candles. Plants were grown in 10.5-cm containers. Plants were pinched once about three weeks after planting. Plants were about eight weeks from unrooted cuttings when the photograph and the detailed botanical description were taken.

In the following description, color references are made to The Royal Horticultural Society Colour Chart, 1995 edition, except where general terms of ordinary dictionary significance are used.

Botanical classification: *Pelargonium×hortorum* cultivar Duecorona.

Parentage:

*Female parent.*—Unknown selection of *Pelargonium× hortorum,* not patented.

*Male parent.*—Unknown selection of *Pelargonium× hortorum,* not patented.

Propagation:

*Type cutting.*—Terminal vegetative cuttings.

*Time to initiate roots.*—Summer: About 5 days at 20° C. Winter: About 7 days at 20° C.

*Time to develop roots.*—Summer: About three weeks at 20° C. Winter: About four weeks at 20° C.

*Root description.*—Fine, fibrous; white in color.

*Rooting habit.*—Freely branching.

Plant description:

*General appearance.*—Upright, somewhat outwardly spreading and rounded plant habit; densely foliated.

*Growth and branching habit.*—Moderately vigorous. Freely branching, about eight lateral branches per plant.

*Plant height.*—About 37 cm.

*Plant width.*—About 20 cm.

*Lateral branches.*—Length: About 30 cm. Internode length: About 3 cm. Texture: Smooth. Color: 144A.

*Foliage description.*—Arrangement: Alternate, single. Length: About 4.8 cm. Width: About 8.1 cm. Shape: Reniform. Apex: Rounded. Base: Cordate. Margin: Crenate. Venation pattern: Palmate. Texture, upper and lower surfaces: Pubescent. Color: Developing foliage, upper surface: 137A to 137B. Developing foliage, lower surface: 137C. Fully expanded foliage, upper surface: 137A; no distinct zonation pattern. Fully expanded foliage, lower surface: 137C. Venation, upper surface: 144A. Venation, lower surface: 144B. Petiole: Length: About 5.1 cm. Diameter: About 2.3 mm. Color, upper and lower surfaces: 143A.

Flower description:

*Flower arrangement.*—Bright red-colored semi-double flowers arranged in rounded hemispherical umbels arising from apical leaf axils. Umbels displayed above and beyond the foliage on peduncles. Flowers rounded in form. Umbels persistent, flowers not persistent. Flowers not fragrant.

*Quantity of flowers.*—Freely flowering; at full flower, plants have about twelve open umbels with about 30 flowers per umbel.

*Flowering season.*—Flowering continuous spring until the autumn. Plants begin flowering about six weeks after planting.

*Flower longevity.*—Flowers last about five to seven days on the plant.

*Umbel size.*—Diameter: About 10.4 cm. Height: About 7 cm.

*Flower size.*—Diameter: About 4.3 cm. Depth (height): About 2 cm.

*Flower buds.*—Length: About 11.6 mm. Diameter: About 7.8 mm. Shape: Ovoid. Color: 144A.

*Petals.*—Quantity per flower: About five or six. Length: About 2.5 cm. Width: About 2.5 cm. Shape: Obovate. Apex: Rounded. Base: Attenuate. Margin: Entire; sinuate. Texture, upper and lower surfaces: Smooth. Color: When opening, upper surface: 43A; towards the base, 61A. When opening, lower surface: 41A to 41B. Fully opened; upper surface: 43A; towards the base, 61A; color does not fade with development. Fully opened, lower surface: 41B.

*Petaloids.*—Quantity per flower: About two to four. Length: About 1.9 cm. Width: About 1.25 cm. Shape: Obovate. Apex: Rounded. Base: Attenuate. Margin: Entire; sinuate. Texture, upper and lower surfaces: Smooth. Color: When opening, upper surface: 43A; towards the base, 61A. When opening, lower surface: 41A to 41B. Fully opened, upper surface: 43A; towards the base, 61A; color does not fade with development. Fully opened, lower surface: 41B.

*Sepals.*—Quantity per flower: About five or six, arranged in a single whorl. Length: About 1.1 cm. Width: About 2.7 mm. Shape: Elongated, tapering. Apex: Apiculate. Margin: Entire. Texture, upper and lower surfaces: Smooth; glabrous. Color, upper surface: 144A. Color, lower surface: 144B.

*Peduncle* (*umbel stem*).—Length: About 17.8 cm. Diameter: About 2 cm. Angle: Mostly erect. Strength: Moderately strong. Texture: Smooth; glabrous. Color: 143A overlain with 59A.

*Pedicel* (*individual flower stem*).—Length: About 2.8 cm. Diameter: About 7.5 mm. Angle: Mostly erect. Strength: Moderately strong. Texture: Pubescent. Color: 144B overlain with 59A.

*Reproductive organs.*—Androecium: Anther quantity per flower: About six to eight. Anther length: About 3 mm. Anther shape: Ovate. Anther color: 61D. Pollen amount: Moderate. Pollen color: 28A to 28B. Gynoecium: Pistil quantity per flower: One. Pistil length: About 8.6 mm. Stigma shape: Five-parted, star-shaped. Stigma color: 61A. Style length: About 4.3 mm. Style color: 144B. Ovary color: 144A.

*Seed/fruit.*—Development of seeds and fruit have not been observed.

Disease/pest resistance: Plants of the new Zonal Geranium have not been observed to be resistant to pathogens and pests common to Zonal Geraniums.

Temperature tolerance: Plants of the new Zonal Geranium have been observed to be tolerant to temperatures ranging from 5 to 40° C.

It is claimed:

1. A new and distinct cultivar of Zonal *Geranium* plant named 'Duecorona', as herein illustrated and described.

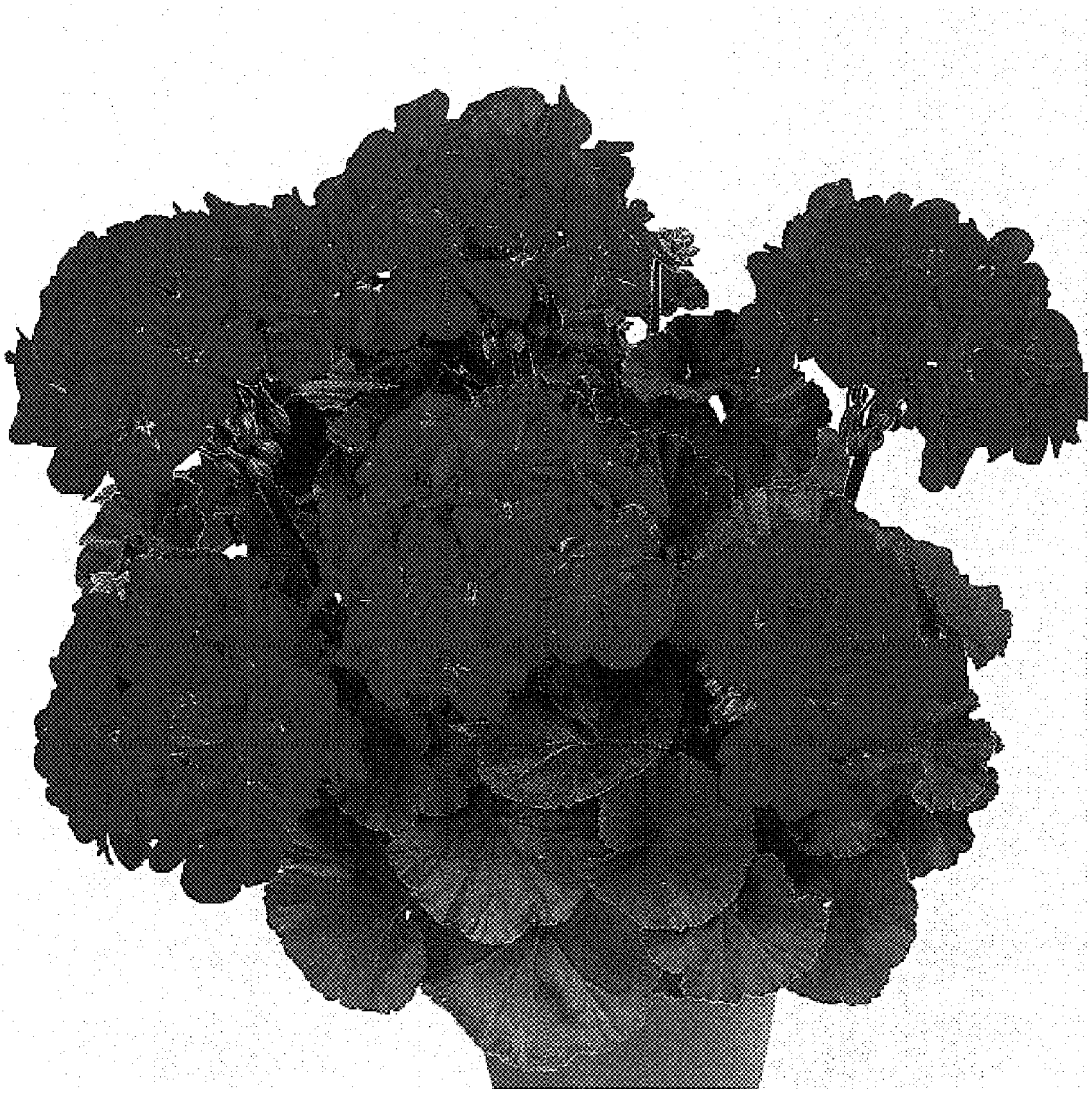

* * * * *